US008936651B2

(12) United States Patent
Yang et al.

(10) Patent No.: US 8,936,651 B2
(45) Date of Patent: Jan. 20, 2015

(54) DECELLULARIZED OMENTUM MATRIX AND USES THEREOF

(71) Applicant: Ehticon, Inc., Somerville, NJ (US)

(72) Inventors: Chunlin Yang, Belle Mead, NJ (US); Qiang Zhang, Annandale, NJ (US); Ilya Koyfman, Ringoes, NJ (US); Ziwei Wang, Bedminster, NJ (US); Daphne Ann Salick Ryan, Manalapan, NJ (US); Robert B. Vetrecin, Stewartsville, NJ (US); Philip M. Steele, Allen, TX (US)

(73) Assignee: Ethicon, Inc., Somerville, NJ (US)

( * ) Notice: Subject to any disclaimer, the term of this patent is extended or adjusted under 35 U.S.C. 154(b) by 140 days.

(21) Appl. No.: 13/804,681

(22) Filed: Mar. 14, 2013

(65) Prior Publication Data

US 2014/0271784 A1 Sep. 18, 2014

(51) Int. Cl.
*A61L 27/36* (2006.01)
*A61K 35/38* (2006.01)
*B29C 43/00* (2006.01)
*B29C 43/52* (2006.01)

(52) U.S. Cl.
CPC ............... *A61K 35/38* (2013.01); *B29C 43/003* (2013.01); *B29C 43/52* (2013.01)
USPC ........................................ 623/23.72; 435/1.3

(58) Field of Classification Search
CPC ............ A61L 27/3633; A61L 27/3683; A61L 27/3687; A61L 27/3691
See application file for complete search history.

(56) References Cited

U.S. PATENT DOCUMENTS

| 4,776,853 A | 10/1988 | Klement |
| 4,801,299 A | 1/1989 | Brendel |
| 2009/0163990 A1 | 6/2009 | Yang |

OTHER PUBLICATIONS

Gilbert, Thomas W., Tiffany L. Sellaro, and Stephen F. Badylak. "Decellularization of tissues and organs." Biomaterials 27.19 (2006): 3675-3683.*
Crapo, Peter M., Thomas W. Gilbert, and Stephen F. Badylak. "An overview of tissue and whole organ decellularization processes." Biomaterials 32.12 (2011): 3233-3243.*
Shrager, Joseph B., et al. "Omentum is highly effective in the management of complex cardiothoracic surgical problems." The Journal of thoracic and cardiovascular surgery 125.3 (2003): 526-532.*

* cited by examiner

*Primary Examiner* — David J Blanchard
*Assistant Examiner* — Peter Anthopolos

(57) ABSTRACT

Methods for defatting omentum and processes for preparing an acellular omentum, i.e., devitalized or decellularized omentum, comprising extracellular matrix for implantation into a mammalian system. Constructs for medical applications comprising decellularized omentum are also described. More specifically, mesh reinforced omentum biomatrix for soft tissue repair is described.

19 Claims, 3 Drawing Sheets

DECELLULARIZED OMENTUM MATRIX AND USES THEREOF

FIELD OF THE INVENTION

The invention relates generally to the field of biomatrix for tissue repair and regeneration. The invention concerns methods for extracting fat from omentum, processes for preparation of decellularized omentum, and the application of decellularized omentum for tissue repair and tissue engineering.

BACKGROUND OF THE INVENTION

Extracellular matrix (ECM) is an important structural component of connective tissues. ECM elaborated by cells creates microenvironments that these and other cells will respond to, by differentiating or maintaining their differentiated state. ECM provides a substrate for organization of cells which adhere to it.

Tissue based ECM biomaterial and devices are used for a variety of medical applications, such as heart valves, porcine SIS, human dermis and bovine pericardium. The application of decellularized tissues as tissue engineering scaffolds for regenerative medicine, however, is limited due to a lack of vascular extracellular matrix components for facilitating angiogenesis, which is vital for tissue ingrowth and the viability and functionality of seeded cells. Tissue that is highly vascularized and rich in vascular extracellular matrix components maintained during the decellularization process would be welcomed in the art.

The greater omentum is the largest peritoneal fold covering the intra-abdominal organs. The greater omentum is highly vascularized, is usually thin and elastic, and always contains some fat. As such, the greater omentum has been used in clinical applications, such as intestinal surgery, thoracic esophageal surgery, chronic, non-healing skin wounds, hernia and pelvic floor repair, bladder repair, and the like.

Because the vascular extracellular matrix components of decellularized omentum can serve as a substrate for neovascularization, omentum is a desired material for clinical application. The fat within the omentum, however, is difficult to remove using methods and procedures known in the art for decellularizing soft mammalian tissue. Thus, effective use of decellularized omentum for biomatricies, including as a tissue based ECM biomaterial is limited because, in part, the processes and methods for devitalizing tissue described in the art cannot effectively extract the fat from omentum.

BRIEF SUMMARY OF THE INVENTION

We disclose a method for defatting omentum by providing an omentum, dehydrating the omentum, defatting the omentum by compressing the omentum under increased temperature and pressure for a sufficient amount of time to remove greater than 50 percent by weight of the fat from the omentum; further defatting the omentum by contacting the omentum with at least one extraction solvent and extracting the residual fat from the omentum to provide a defatted omentum having less than 5 percent by weight of fat. Optionally, the omentum may be mechanically processed into pieces in the size of from about 1 mm to about 5 mm before dehydrating, before the compression defatting step, or before the extraction solvent defatting step. Furthermore, the omentum may be decellularized, disinfected, and sterilized.

DETAILED DESCRIPTION OF THE INVENTION

Figure 1:
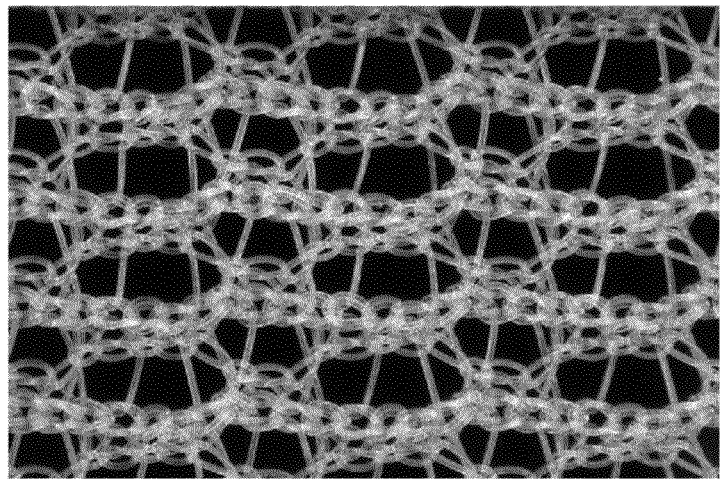
FIG. 1. Photographic image of a PDO mesh.

We describe herein a method for defatting omentum comprising providing an omentum, dehydrating the omentum, defatting the omentum by compressing the omentum under increased temperature and pressure for a sufficient amount of time to remove greater than 50 percent by weight of the fat from the omentum; further defatting the omentum by contacting the omentum with at least one extraction solvent and extracting the residual fat from the omentum to provide a defatted omentum having less than 5 percent by weight of fat. Optionally, the omentum may be mechanically processed into pieces in the size of from about 1 mm to about 5 mm before dehydrating, before the compression defatting step, or before the extraction solvent defatting step. Furthermore, the omentum may be decellularized, disinfected, and sterilized.

Omentum may be harvested from mammalian species, such as human, swine, bovine, goat, and the like. Following tissue harvesting, the tissue can be either placed in 0.9 percent saline for immediate processing or stored for later use, preferably at a temperature of about −20° C. to about −80° C.

Defatting for purposes of the invention refers to extracting the lipid moiety in the tissue.

Decellularization, also referred to as devitalization in the art, for purposes of the invention refers to removing the cellular components of an isolated organ, or a part of an organ, while maintaining the structural extracellular matrix components. The terms decellularized or decellurization and devitalized or devitalization shall be used herein interchangeably. Devitalized tissue is essentially free from reproductively and/or metabolically viable cells. Omentum devoid of reproductively viable cells, however, could contain metabolically dead cells that might be visible in histology sections appearing similar to a metabolically live cell when viewed with the use of a microscope. Furthermore, residual cellular remnants, including but not limited to nucleic acids, DNA, small molecular weight proteins, lipids, and polysaccharides may remain. Decellularized omentum or devitalized omentum refers to omentum having all, some, or a substantial amount of the nuclear and cellular components removed.

The omentum is first dehydrated prior to defatting. The dehydration is accomplished by freeze-drying the omentum by lyophilization. Optionally, the omentum may be submerged in a lyoprotectant solution prior to lyophilization to prevent protein denaturation and/or aggregation during the lyophilization process. Typically, lyoprotectant (freeze-drying) solutions are buffered solutions which contain excipients which help to protect the protein structure during freezing and drying. Typically, the excipients may include a combination of the following; sugars and polyols (trehalose, sucrose, mannitol), synthetic polymers (dextran, polyvinyl alcohol), proteins (BSA), non-aqueous solvents (dimethyl sulfoxide, dimethylformamide), surfactants (polysorbate 80, tween 20), amino acids (glycine, proline) and other excipients including salts, amine compounds and metals to name a few. The omentum is dehydrated using a standard lyophilization cycle for the removal of water. Alternatively, the omentum may be dehydrated using solvent extraction techniques as described in US Patent Publication number US20090163990, incorporated herein by reference.

Next, the lipid or fat component of the omentum is removed using a first fat extraction step by mechanical compression process where the majority of lipids are removed, followed by a second fat extraction step by solvent extraction where the remaining lipids are removed. In the compression process, freeze-dried omentum tissue is loaded in a cylindrical compression device having a collection pan to collect the liquid fat. The compression device assembly is placed in between the plates of a mechanical press preheated to a temperature which allows for easier flow of the liquid fat out of the omentum during compression without damaging the tissue, for example in the range of from about 37° C. to about 40° C. While using higher temperatures increases the defatting efficiency and is within the scope of this invention, the tissue is maintained at a temperature in the range of from about 37° C. to about 40° C. to minimize degradation of the omentum tissue. The omentum is held at the desired temperature for a sufficient length of time for the tissue to equilibrate to the set temperature, for example in the range of about 10 minutes to about 40 minutes. The compression force is then slowly applied. Fat in viscous liquid form is squeezed out of the mold and collected in the collection pan. The compression continues for a time sufficient to remove a substantial amount of fat from the omentum, for example from about 20 minutes to about 120 minutes. The compression force is increased gradually to about 24,000 lbs of pressure; higher compression forces can also be used depending upon the pressure limits of the press. The mold assembly is removed from the press and the compressed omentum is de-molded. A compressed "cake" of omentum tissue is obtained. A substantial amount of fat is removed from the omentum during this compression step, for example at least 50 percent by weight of the fat is removed. In one embodiment, fat is removed from the omentum in the range of from about 50 percent to 85 percent by weight of the omentum.

The compressed omentum is then further defatted using solvent extraction in a second fat removal step. The fat is extracted from the omentum by extraction using one or more extraction solvents. The extraction solvents may be non-polar solvent, polar solvent, such as polar aprotic solvent, or combinations thereof. Examples of non-polar solvents are nonpolar organic solvents such as hexane, cyclohexane, xylene, benzene, toluene, ethyl acetate and combinations thereof. Polar solvents useful for the extraction solvent include acetone, dioxane, acetonitrile and combinations thereof. In an embodiment, the extraction solvent is selected from acetone, hexane, cyclohexane, xylene and combinations thereof. The extraction solvent may have about 50 percent to about 90 percent nonpolar solvent, such as hexane, cyclohexane, xylene and combinations thereof and about 10 percent to about 50 percent polar solvent, such as acetone. In certain embodiments, the extraction solvent may have about 20 percent to about 50 percent acetone and about 80 percent to about 50 percent cyclohexane.

Fat extraction is conducted by contacting the dehydrated compressed omentum with extraction solvents for a period of time. Additional solvent fat extraction steps may be conducted using the same or different extraction solvent(s) under the same or different conditions for the same or different periods of time. In one embodiment, the fat extraction may include contacting the dehydrated compressed omentum with one or more extraction solvent(s), or combinations of the extraction solvents, for a period of time of at least about 30 minutes, such as at least about 60 minutes up to about 24 hours, or up to about 48 hours, or more. Further embodiments involve submerging the dehydrated compressed omentum in the extraction solvent. During each extraction step the solvent may be changed or refreshed periodically. The use of the compression process significantly reduces the amount of the solvent used, thus yielding a greener and cheaper defatting process. The amount of solvent used in the solvent extraction defatting step is reduced by the percentage of fat removed during the compression step. For example, if 50 percent of the fat is removed from the omentum during the compression process, then 50 percent less solvent is required for the solvent extraction step.

In one embodiment, the fat extraction is conducted with a plurality of solvent fat extracting steps. For example, the dehydrated compressed omentum is contacted with a first extraction solvent, such as a polar solvent, such as a polar aprotic solvent, for at least about 30 minutes, typically for about 30 minutes to about 24 hours. The dehydrated compressed omentum may be fully submerged in the first extraction solvent. In an aspect of the invention, the weight ratio of dehydrated omentum to first extraction solvent is about 1:3 to about 1:30, such as about 1:5 to about 1:15. In one embodiment, the first extraction solvent is acetone. After the first extraction step the dehydrated compressed omentum is contacted with a second extraction solvent, such as a mixture of about 30 percent to about 50 percent polar solvent and about 50 percent to about 70 percent non-polar solvent for a period to time of at least about 60 minutes, such as about 60 minutes to about 24 hours. In an embodiment, the second extraction solvent has about 30 percent to about 50 percent hexane and about 70 percent to about 50 percent acetone. The dehydrated compressed omentum may be fully submerged in the second extraction solvent. In an aspect of the invention, the weight ratio of dehydrated compressed omentum to second extraction solvent is about 1:3 to about 1:30, such as about 1:5 to about 1:15. Further solvent fat extraction steps may be continued in this manner until the fat is removed from the omentum in the desired amount.

Alternatively, the solvent fat extraction step may be accomplished using supercritical carbon dioxide ($CO_2$) extraction. In one embodiment, supercritical $CO_2$ is used to extract residual fat from the dehydrated, compressed tissue. A range of extraction conditions (such as temperature, pressure and flow rate and extraction time) can be used. The temperature range is from about 32° C. to about 90° C., although in one embodiment the temperature is in the range of from about 60° C. to about 85° C. The carbon dioxide flow rate is in the range of from about 20 g/min to about 50 g/min; higher flow rates can be obtained in the extraction apparatus using a higher capacity $CO_2$ pump. The pressure of the extraction is in the range of from about 110 bar to about 640 bar, while higher extraction can be achieved in an extraction system where the equipment pressure rating is higher. The combined approach of a mechanical compression process and a supercritical $CO_2$ extraction process effectively removes the majority of the fat (lipids) from the omentum, resulting in a defatted omentum that contains less than 2 percent lipids by weight. This approach will in turn completely eliminate the use of organic solvents which is advantageous for use of defatted omentum in medical applications.

Optionally, a small amount of a co-solvent(s) (i.e., hexane or cyclohexane) can also be used to increase the extraction efficiency. The addition of the co-solvent(s) can also serve to reduce extraction temperature, pressure, carbon dioxide flow rate, and/or extraction time.

After the solvent defatting step or steps, the defatted omentum is optionally re-hydrated. The defatted omentum maybe re-hydrated by contacting the defatted omentum with a re-hydration solvent, such as alcohol or a solution of alcohol in water, such as an alcohol solution having from about 60 percent to about 70 percent alcohol. Low molecular weight alcohols, such as methanol, ethanol, isopropanol, propanol and combinations thereof may be used. In an embodiment of the invention, re-hydration is conducted in one or more re-hydration treatments, such as two treatments. In an aspect of the invention, the weight ratio of defatted omentum to re-hydration solvent in all or some of the re-hydration treatments is about 1:5 to about 1:100, such as about 1:10 to about 1:25. The defatted omentum may be contacted with the re-hydration solvent for at least 30 minutes, such as about 30 minutes to about 72 hours, and may be fully submerged in the re-hydration solvent. Additional rehydration steps may be performed as described above to rehydrate the defatted omentum.

In one embodiment, the omentum may be mechanically processed into small pieces by conventional means such as homogenization, grinding, manually cutting, solution homogenization, cryomilling, cold blending, and the like. The smaller pieces of omentum tissue enables better extraction efficiency in all solvent defatting and decellularization steps. Mechanically processing the omentum into small pieces may be performed before or after any step in the process, for example, prior to dehydration, prior to the first defatting step (compression), prior to the second defatting step (solvent extraction), prior to re-hydration, and/or prior to decellularization, devitalization, or sterilization. The omentum tissue is reduced into small pieces where the longest dimension of the tissue is in the range of about 1 mm to about 5 mm. In one embodiment, the omentum tissue is homogenized by passing the omentum through a meat grinder one or more times where the omentum tissue is reduced to much smaller sizes. The homogenization step also serves to "normalize" the tissue and make the tissue more uniform.

The defatted omentum may also be disinfected to remove contaminants. In an embodiment, the defatted decellularized omentum is contacted with a disinfection solution for a sufficiently effective period of time to disinfect the decellularized omentum, such as at least about 30 minutes, typically about 1 hour to about 12 hours. The defatted decellularized omentum may be fully submerged in the disinfection solution. The disinfection solution may have alcohol, or an alcohol in water solution, and may also include acid. The disinfection solution may include one or more of the following: ethanol, methanol, isopropanol, propanol, hydrogen peroxide, peracetic acid and combinations thereof. In an embodiment, the disinfection solution has ethanol, such as an 80 percent ethanol solution, and peracetic acid. Optionally, the defatted decellularized omentum can be washed one or more times with ultrapure water.

The defatted disinfected omentum is then decellularized by decellularization processes known to one skilled in the art. In one embodiment, the defatted omentum may be decellularized by solubilization of the nuclear and cytoplasmic components. For example, the defatted omentum may be immersed in a decellularization buffer, such as one having non-ionic detergent and metal salt dissolved in acid for a period of time, typically at least about 30 minutes. Non-ionic detergents useful in the invention include polysorbates, such as those sold under the tradename TWEEN 80 by Sigma-Aldrich, St. Louis, Mo.; ethoxylated alcohols, such as those sold under the tradename TRITON X-100 by Sigma-Aldrich, St. Louis, Mo.; and polyethanols, such as NP 40 and octylphenoxypolyethoxyethanol sold under the tradename IGEPAL CA-630 by Sigma-Aldrich, St. Louis, Mo.; and combinations thereof.

Metal salts that may be used include magnesium chloride, phosphate, acetate and citrate, and combinations thereof and these metal salts are typically dissolved in Tris-HCl. For example, the decellularization buffer may include TRITON® X-100 (1 percent w/V) and $MgCl_2$ (1 percent) dissolved in 50 mM Tris-HCl (pH 7.2). The defatted omentum is then removed from the decellularization buffer and optionally may be contacted with an enzyme solution, such as one having endonuclease, such as benzonase, and the components of the decellularization buffer. In an embodiment, the defatted omentum is spun in the enzyme solution for a period of time, such as at least about 20 hours, typically from about 20 hours to about 48 hours. The defatted omentum is then washed one or more times, such as twice, in a rinsing solution, such as one having acid, metal salt and nonionic detergent. The acid, metal salt and nonionic detergent may be the same as the materials discussed above, including the combination of Tris-HCl, $MgCl_2$ and TRITON® X-100. Subsequently, the omentum is contacted with a cell extracting solution having salts, such as NaCl and EDTA, and non-ionic detergent, such as TRITON® X-100, for a period of time, such as at least about 1 hour, typically from about 1 hour to about 48 hours. Examples of typical decellularization processes are further described in U.S. Pat. Nos. 4,776,853 and 4,801,299 incorporated herein by reference in their entirety. In another embodiment, the defatted omentum may be decellularized by solubilization of the nuclear and cytoplasmic components using a strong base solution. For example, the defatted omentum may be immersed in 0.1N NaOH typically for at least about 6 hours followed by extraction with non-ionic detergents solution. Non-ionic detergents useful in the invention include polysorbates, such as TWEEN® 80, ethoxylated alcohols, such as TRITON® X-100, and polyethanols, such as NP 40 and IGEPAL® CA-630 and combinations thereof. The defatted decellularized omentum can be washed one or more times with ultrapure water.

The defatted decellularized omentum may be applied in tissue engineering and regeneration of internal organs, such as kidney, liver, spleen and bladder. The defatted decellularized omentum can also be used for repair and regeneration of skeletal tissues, such as bone, cartilage and tendon. Other uses for the defatted decellularized omentum include soft tissue reinforcement and repair in combination with biocompatible meshes, such as dural grafting, hernia repair, and pelvic floor repair; nerve regeneration, such as a tubular structure for peripheral nerve regeneration; tissue augmentation; delivery of cells and bioactives; chronic wound repair; and bone repair. These uses and applications of the defatted decellularized omentum are illustrative of several potential uses and should not be construed as limiting the types of uses and applications for the defatted decellularized omentum prepared by the methods and processes described herein.

In another embodiment, defatted decellularized omentum can be formulated in to porous scaffolds in which stem cells, such as adipose tissue derived stem cells and bone marrow stem cells, are seeded. The cell seeded scaffolds have utility for tissue regeneration and repair. In a further embodiment, adipose tissue derived stem cells seeded defatted decellularized scaffolds can be used for myocardial infarction repair.

The defatted decellularized omentum can be combined with synthetic constructs to make reinforced constructs. For example, the defatted decellularized omentum matrix can be used as a scaffold structure for implantation in a mammalian body, such as scaffold for tissue repair. It can be further enhanced by bioactives, cells, small molecules, minced tissue and cell lysates. The defatted decellularized omentum can be lypophilized with polymers to make foam or heat melted into a film or mesh to name a few additional uses for the decellularized omentum. Further, fibers may be electrostatically spun onto the omentum and used "as is" or with synthetic constructs to make reinforced structures. In one embodiment, defatted decellularized omentum is formulated into a tubular structure with or without reinforcement. The tubular omentum matrix can be seeded with endothelial cells in which the defatted decellularized omentum serves as a cell attachment scaffold and growth promoting substrate. An endothelial cell seeded defatted decellularized omentum has utility as a building block material for vascular reconstruction.

In another embodiment, defatted decellularized omentum can be co-cultured with human kidney derived cells (hKDC) in which the defatted decellularized omentum serves as a cell attachment scaffold and growth promoting substrate. An hKDC seeded defatted decellularized omentum has utility as a building block material for kidney tissue engineering applications.

In a further embodiment, defatted decellularized omentum can be co-cultured with urothelial cells in which the defatted decellularized omentum serves as a cell attachment scaffold and growth promoting substrate. Urothelial cells seeded onto defatted decellularized omentum have utility as a building block material for bladder reconstruction.

Bioactive agents may be incorporated within and/or applied to the tissue scaffolds, and/or applied to the viable minced tissue that is then incorporated to the scaffolds. Preferably, the bioactive agent is incorporated within or coated on the scaffold prior to the addition of viable tissue to the scaffold. The bioactive agent(s) can be selected from among a variety of effectors that, when present at the site of injury, promote healing and/or regeneration of the affected tissue. In addition to being compounds or agents that promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (sold under the tradename INTERCEED and SURGICEL, available from Ethicon, Inc., Somerville, N.J., USA), compounds or agents that suppress the immune system (e.g., immunosuppressants), and combinations thereof.

By way of non-limiting example, other types of effectors present within an implant of the invention having the defatted decellularized omentum can include heterologous or autologous growth factors, proteins (including matrix proteins), peptides, antibodies, enzymes, platelets, platelet rich plasma, glycoproteins, hormones, cytokines, glycosaminoglycans, nucleic acids, analgesics, viruses, virus particles, cell types and combinations thereof. One or more effectors of the same or different functionality may be incorporated within the implant. Many different types of heterologous or autologous growth factors known to promote healing and/or regeneration of injured or damaged tissue may be incorporated directly into the scaffold, or alternatively, the scaffold can include a source of growth factors, such as for example, platelets.

Bioactive agents, may further include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short term peptides, bone morphogenic proteins, glycoprotein and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGF-beta I-III), parathyroid hormone, parathyroid hormone related peptide, bone morphogenic proteins (e.g., BMP-2, BMP-4; BMP-6; BMP-12), sonic hedgehog, growth differentiation factors (e.g., GDF5, GDF6, GDF8), recombinant human growth factors (e.g., MP52), cartilage-derived morphogenic proteins (CDMP-1)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids.

Suitable effectors likewise include the agonists and antagonists of the agents described above. The growth factor can also include combinations of the growth factors described above. In addition, the growth factor can be autologous growth factor that is supplied by platelets in the blood, which may have various growth factors normally associated with platelets. If other such substances have therapeutic value in the orthopedic field, it is anticipated that at least some of these substances will have use in the invention, and such substances should be included in the meaning of "bioactive agent" and "bioactive agents" unless expressly limited otherwise.

The defatted decellularized omentum can further be formulated into composite scaffolds in combination with biocompatible synthetic or natural polymers. In one embodiment, the decellularized omentum matrix can be reinforced to enhance its mechanical strength. The reinforcement component can be a film with or without pores, fiber structure, foam and the like. The reinforced defatted decellularized omentum can be formulated into films, matrix and tubular structures with and without matrix in the lumen for tissue engineering and regenerative medicine in combination with cells, minced tissue, bioactives, and other tissue engineering scaffolds.

Varieties of biocompatible, bioabsorbable polymers can be used to prepare the non-woven tissue engineering scaffolds and the mesh used to reinforce the defatted decellularized omentum according to the invention. Examples of suitable biocompatible, bioabsorbable polymers include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biopolymers, and blends thereof. Aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof.

Varieties of biocompatible non-absorbable polymers can also be used to prepare the non-woven tissue engineering scaffolds and the mesh according to the invention. Suitable biocompatible non-absorbable polymers include, but are not limited to cotton, linen, silk, nylon, such as nylon 6-6 and aromatic polyamides, such as those commercially available under the tradenames KEVLAR or NOMEX from E. I. du Pont de Nemours and Company, Willmington, Del., polyesters, such as poly(ethylene terephthalate), fluoropolymers, such as polytetrafluoroethylene, fluorinated poly(ethylenepropylene) (FEP) and polyvinylidene fluoride (PFA), polyolefins, such as polyethylene and polypropylene, polyurethanes and combinations thereof. An example of a mesh made from non-absorbable polymers is a polypropylene mesh, such as that sold under the tradename PROLENE available from Ethicon, Inc., Somerville, N.J.

Varieties of biocompatible natural biopolymers can also be used for the non-woven tissue engineering scaffolds and the mesh having the decellularized omentum in accordance with the invention. Suitable natural polymers include, but are not limited to proteins such as, collagen, elastin, keratin, silk, glucosaminoglycans (GAGs), thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, and atelocollagen; polysaccharides such as, starch, pectin, cellulose, alkyl cellulose (e.g. methylcellulose), alkylhydroxyalkyl cellulose (e.g. ethylhydroxyethyl cellulose), hydroxyalkyl cellulose (e.g. hydroxyethyl cellulose), cellulose sulfate, salts of carboxymethyl cellulose, carboxymethyl cellulose, carboxyethyl cellulose, chitin, carboxymethyl chitin, hyaluronic acid, salts of hyaluronic acid, alginate, cross-linked alginate alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyglucuronic acid, and derivatives; polynucleotides such as, ribonucleic acids, deoxyribonucleic acids, and combinations thereof.

In one embodiment the natural polymer is collagen. In yet another embodiment the natural polymer may be obtained from decellularized tissue. The decellularized tissue may be obtained from autogeneic tissue, allogeneic tissue or xenogeneic tissue. Suitable decellularized tissues include, but are not limited to skin, periosteum, perichondrium, synovium, fascia, mesenter, bone, sinew, and the like. In another embodiment, the natural polymer is a polysaccharide. In yet another embodiment, the polysaccharide is hyaluronic acid.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example 1

Omentum Compression and Supercritical $CO_2$ Defatting Process

The porcine omentum, obtained from a Specific Pathogen Free accredited farm (Tissue Source, LLC, Lafayette, Ind.), was first washed with saline followed by tissue trimming to remove extraneous tissue. Next, the omentum was washed three times with saline followed by three washes with endotoxin free water. Subsequently, the omentum was freeze-dried in a lyophilizer using a typical cycle for the removal of water (see Table 1 in Example 2). 157 g of freeze-dried omentum was first heated on the bottom platen of a hydraulic press (sold by Carver, Inc., Wabash, Ind., Model 4386) set at 37.2 degrees Celsius on an aluminum foil for 20 minutes and then loaded into a cylindrical compression device having a collection pan to collect the liquid fat and compressed for about 30 minutes with compression forces increased up to about 22,000 lbs. The compressed "cake" weighed in at 27.9 g, a weight (lipid) loss of 82.2 percent.

The compression de-fatted "cake" was loosened up and then loaded in a supercritical carbon dioxide extraction vessel and extracted to remove the remaining fat. The extraction was done in a supercritical carbon dioxide extraction system Model SPE-500MR (Thar Technologies, Inc., Pittsburgh, Pa.) equipped with a 1.0 liter extraction vessel. About 29.5 g of the compression de-fatted material was extracted for about nine hours at 85 degrees Celsius, 600 bar with a $CO_2$ flow rate of 25 g/min.

Residual lipid content was measured using an FTIR method. Briefly, residual lipid was extracted from the sample with a chloroform-methanol (2:1) solvent and with the sample to solvent ration of 1/100 in a 15 mL vial. The extract solution was filtered through a glass wool plugged pipet. The filtrate was added to a new 15 mL vial and allowed to dry using a nitrogen gas stream. The residual lipid was redissolved in 1 mL of hexane. FTIR was measured on the sample using a Perkin-Elmer Spectrum 1000 equipped with a KBr sealed cell for liquid sampling having a 1 mm pathlength. The FTIR was measured in the range of 1830-1580 $cm^{-1}$. The absorbance was then measured at 1750 $cm^{-1}$ and compared against a standard curve of porcine omentum fat in hexane which was prepared using at least four different solution concentrations. The supercritical $CO_2$ extracted material had a residual lipid content of 1.5 wt percent.

Example 2

Lyoprotection Of Omentum Prior to Freeze-Drying

In this example we add an optional, additional lyoprotection step to prevent potential protein aggregation and/or denaturation of the porcine omentum during lyophilization. Porcine omentum was obtained and washed as described in Example 1. The porcine omentum was soaked in a lyoprotectant solution prior to lyophilization. Briefly, the omentum was first washed with saline followed by tissue trimming to remove extraneous tissue. Next, the tissue was washed three times with saline followed by three washes with endotoxin free water. After extensive washing, the trimmed omentum was introduced to a solution of 50 millimolar citrate pH 6 buffer containing 10 percent sucrose and 0.1 percent polysorbate 80. To prepare 4 liters of citrate buffer, 38.4 grams of citric acid (molecular weight=192.12 grams per mole) to 3800 milliliters of endotoxin free water. The pH was then adjusted to 6 using concentrated sodium hydroxide. The remaining endotoxin free water was introduced to obtain a final volume of 4000 milliliters. Next, approximately 500 milliliters of 50 millimolar citrate buffer pH 6 was transferred to a sterile container to be used in future steps of solution preparation. To the 3500 milliliters of citrate buffer, 400 grams of sucrose was introduced and allowed to dissolve followed by the addition of 50 millimolar citrate buffer to 3800 milliliters. To the solution containing the sucrose in 50 millimolar citrate buffer pH 6, 4 milliliters of polysorbate 80 was introduced. The solution was diluted with 50 millimolar citrate buffer pH 6 to 4000 milliliters. The lyoprotectant solution was introduced to the omentum at a weight to volume ratio of 500 g per 1 liter, respectively. The omentum was allowed to soak at room temperature on a rocker platform for 2 hours. After soaking, excess lyoprotectant solution was removed from the omentum using a strainer with mild compression. The lyoprotectant soaked omentum was then lyophilized following the cycle shown in Table 1.

TABLE 1

| Temperature (° C.) | Time (minutes) | Pressure (mTorr) |
|---|---|---|
| −40 | 120 | 100 |
| −20 | 1200 | 100 |
| −5 | 600 | 100 |
| 5 | 600 | 50 |
| 20 | 60 | 50 |
| 20 | 120 | 50 |

Example 3

Preparation of Acellular Omentum Biomatrix by Solvent Defatting, and then Decellularization FAT EXTRACTION: Porcine omentum, obtained from a Specific Pathogen Free accredited farm (Tissue Source, LLC, Lafayette, Ind.), was placed in 0.033 M EDTA with 0.9 percent saline solution after harvest. After rinsing in the 0.9 percent saline solution 3 times (700 ml saline/kg of omentum) followed by rinsing with endotoxin-free water five times (1.5 liter water/kg omentum) to rinse off blood and trim out other extraneous tissue, the omentum was submerged in 70 percent ethanol for 30 minutes. Then fresh 70 percent ethanol was used to soak the tissue overnight, with both 70 percent steps using 1.5 liter/kg omentum. After draining the ethanol, the omentum was processed by passing through a meat grinder sold under the tradename WARING PRO by Conair Corporation, Stamford, Conn. (Model MG105). The ground tissue was then dehydrated in 100 percent ethanol with two changes into fresh ethanol, first for 90 minutes and the second for 30 minutes, both using 1.5 liter ethanol per kilogram of omentum. The tissue was then transferred to acetone for two washes using fresh solution with first wash being 90 minutes and the second 45 minutes. Subsequently, the tissue was placed in a 50:50 acetone-hexane mixture for 120 minutes; the tissue was then placed in a 20:80 mixture of the same solvents for overnight (14 hours) followed by two changes of fresh solvents of the same ratio, for 120 minutes and 60 minutes respectively. The solution to omentum ratio remained to be 1.5 liter per kilogram omentum for all the above washes. The tissue was then washed in acetone twice with 15 minutes each with a solvent to tissue ration of 1 liter per kg omentum. The tissue was then transferred to 100 percent ethanol for three washes for a total of 135 minutes using fresh solvent for each wash using 1 liter ethanol per kg of omentum for each wash. All the washing steps above were done in stainless steel containers which were placed on an orbital shaker operating at 80-100 rpm.

DISINFECTION: After filtering out the ethanol, the tissue was transferred to 500 ml centrifuge tubes and into a disinfection solution having 80:20 water:ethanol (200 proof) with 0.15 percent peracetic acid for 30 minutes using 1.5 liter solution per 100 gram of defatted omentum material (wet weight). The disinfected material was then washed in DPBS twice (30 minutes each wash with fresh solution and 1 liter solution per 100 g tissue) to neutralize. After every wash, the tissue was separated from the washing solution by centrifugation using a benchtop centrifuge sold under the tradename Allegra 6R by Beckman Coulter, Inc., Indianapolis, Ind. for 10 minutes at 3000 rpm.

DECELLULARIZATION: The tissue was then immersed in a 0.1 N NaOH solution for 17 hours (using 1.5 liter solution per 100 g tissue) followed by four short DPBS washes with 15-20 minutes each wash (1 liter solution per 100 g tissue for each wash). Following the NaOH treatment, the tissue was immersed in a decellularization buffer solution having TRITON® X-100 (1 percent w/V; a nonionic detergent) dissolved in 50 mM Tris-HCl (pH 7.2) overnight with 1.5 liter solution per 100 g of tissue. This was followed by five short washes (15 minutes each) using endotoxin-free water at 1 liter water per 100 g of tissue for each wash. The tissue was then placed in 1M NaCl solution for 3 washes, for 30, 60 and 30 minutes respectively, following which the tissue was washed with endotoxin-free water (6 times, 20 minutes each). All the NaCl and water washes used 1 liter solution per 100 g tissue ratio. After straining out the water, the tissue was lyophilized using a two-day drying cycle (Table 1), after which a dry acellular omentum biomatrix was obtained. The residual lipid analysis was performed using an FTIR method as described in Example 1. The results showed that the material had very low residual lipid level (0.13 wt. percent). Residual DNA in the sample was determined using a fluorescence emission method. DNA was extracted from a 10 mg sample by an using 300 microliters of extraction buffer (0.25 mL of Tris buffer, 1.0 mL of 0.5M (pH 8) EDTA, 0.05 mL of 10 mg/mL proteinase K solution, and 3.7 mL DI water to a final volume of 5 mL) in a microtube and heating in an oven at 55° C. for 15-17 hours. 300 microliters of chloroform were added once the solution cooled and was mixed by inverting the microtube several times. After centrifugation, a fluorometer sold under the tradename QUBIT by Life Technologies Corporation, Grand Island N.Y., along with a dsDNA BR assay kit sold under the tradename QUBIT by Life Technologies Corporation, Grand Island N.Y., were used to measure the fluorescence of 5 microliters of sample supernatant and at least four calibration solutions. DNA found in the extract was determined based on fluorescence emission due to DNA-binding dye. The DNA test showed that the sample had very low levels of residual DNA (0.02 wt. percent). Histology results (by HE staining) also showed that there were no cellular in the material.

Example 4

Preparation of Acellular Omentum Biomatrix by Lyophilization with Lyoprotectant, Grinding, Compression, Solvent Defatting and then Decellularization LYOPHILIZATION, GRINDING, COMPRESSION: Porcine omentum, obtained from a Specific Pathogen Free accredited farm (Tissue Source, LLC, Lafayette, Ind.), was placed in 0.033 M EDTA with 0.9 percent saline solution after harvest. After rinsing in the 0.9 percent saline solution 3 times (700 ml saline/kg of omentum) followed by rinsing with endotoxin-free water four times (1.5 liter water/kg omentum) to rinse off blood and trim off other extraneous tissue, the omentum was soaked in a lyoprotectant solution (50 mM citrate, 10 percent sucrose, 0.1 percent polysorbate 80) using 2 liter solution per kilogram omentum ratio for 120 minutes. After draining out the solution, the tissue was dried in a lyophilizer using a two-day cycle (Table 1). The dehydrated tissue was then homogenized by passing through a meat grinder sold under the tradename WARING PRO by Conair Corporation, Stamford, Conn. (Model MG105), twice. The ground tissue was then loaded into a stainless steel cylindrical compression device having a collection pan to collect the liquid fat (150 g for each batch) and then the compression device assembly was placed in between the plates of a hydraulic press (sold by Carver, Inc., Wabash, Ind., Model 4386) with temperature set at 37.2 degrees Celsius; after allowing the material to heat at this temperature for about 10 to 40 minutes to allow the material to reach the set temperature, compression force was slowly applied. Fat in viscous liquid form was squeezed out of the mold and collected in the collection pan. The compression continued for about 20 to 40 minutes where the compression force was increased up to about 24,000 lbs; after that, the mold assembly was taken out of the press and the compressed material was de-molded. A compressed "cake" was obtained where about 55-60 wt percent of lipids were removed, as determined by the weight difference between the samples before and after the compression process.

FAT EXTRACTION: The same procedures outlined in Example 3 were used to extract lipids from the omentum tissue, but much smaller amounts of solvents were used, due to the fact that more than 50 percent (by weight) of the fat were already removed in the mechanical compression step; the solvent to tissue ratio was calculated based on the remaining lipid contents therefore only about 45 percent of solvent was used on a per kg omentum basis compared to the amount used in Example 3.

DISINFECTION and DECELLULARIZATION: The same procedures in Example 3 were followed for disinfection and decellularization. At the end of the processes, a dry acellular omentum biomatrix material was obtained. The lipid analysis using an FTIR method (see Example 1) showed that the tissue had very low residual lipid level (0.08 percent). Residual DNA testing using a fluorescence emission method (see Example 3) showed that the material had very low levels of residual DNA (0.004 wt. percent); histology results (by HE staining) also showed that there was no cellular remnants in the material.

Example 5

Preparation of Acellular Omentum Biomatrix by Lyophilization, Compression, Supercritical $CO_2$ Extraction and then Decellularization LYOPHILIZATION and COMPRESSION: Porcine omentum, obtained from a Specific Pathogen Free accredited farm (Tissue Source, LLC, Lafayette, Ind.) was placed in 0.9 percent saline solution after harvest. After rinsing in the saline solution 3 times followed by rinsing with endotoxin-free water four times to rinse off blood trim off and other extraneous tissue, the tissue was dried in a lyophilizer using a two-day cycle (Table 1). The dried tissue was then loaded into a stainless steel compression mold device (150 g for each batch) and then the compression device assembly was placed in between the plates of a hydraulic press (sold by Carver, Inc., Wabash, Ind., Model 4386) with temperature set at 37.2 degrees Celsius; after allowing the material to heat at this temperature for about 10 to 40 minutes to allow the material to reach the set temperature, compression force was slowly applied. Fat in viscous liquid form was squeezed out of the mold and collected in the collection pan. The compression continued for about 20 to 40 minutes where the compression force was increased up to about 24,000 lbs; after that, the mold assembly was taken out of the press and the compressed material was de-molded. A compressed "cake" was obtained where about 80 wt percent of lipids were removed, as determined by the weight difference in the samples before and after compression.

FAT EXTRACTION: The compressed omentum material was processed in a supercritical extraction process to remove fat. The extraction was done in a supercritical fluid extraction system (Model SPE-500MR, Thar Technologies, Inc., Pittsburgh, Pa.) equipped with a 1000 ml extraction vessel. The compressed omentum material was first loaded into the extraction basket; the basket loaded with the samples was then loaded into the extraction vessel with polytetrafluoroethylene (PTFE) o-rings to prevent $CO_2$ from flowing through the gap in between the outside diameter of the basket and the inside diameter of the extraction vessel. Extraction was done at 85 degrees Celsius and 600 bar with total extraction time of 11 hours and a nominal $CO_2$ rate of 40 g/min. When the process was started, the system (at room temperature) was first charged with liquid $CO_2$ and then the $CO_2$ pump was started and the pre-heater and the band heater turned on and both were set at 40 degrees Celsius and the system pressure set at 400 bar in an effort to first remove any possible remaining moisture in the samples. After that, the temperatures were re-set to 85 degrees Celsius and the system pressure was re-set to 600 Bar with $CO_2$ flow rate set at 40 g/min for a total of 11 hours of extraction.

The supercritical $CO_2$ extracted omentum material was soaked in ultrapure water obtained from a water purification system, Milli-Q Integral 3 sold by EMD Millipore Corporation, Billerica, Mass. in a container for 4 hours for re-hydration; then the rehydrated $CO_2$ extracted omentum was homogenized in a blender where the omentum-water mixture was blended for 30 seconds (two 15 seconds blending with 5 seconds break); the process was then repeated. The larger pieces of material were chopped using a pair of scissors before each blending cycle. The homogenized material was then transferred into a 500 ml centrifuge tube with 100 ml of detergent solution added per 1 gram of post $CO_2$ dry tissue weight (TRITON® X-100, 1 percent w/V dissolved in 50 mM Tris-HCl (pH 7.2)). The detergent wash was continued for 15 hours by placing the centrifuge tube on an orbital shaker set at 120 rpm. After the detergent wash, the material was centrifuged in a benchtop centrifuge sold under the tradename Allegra 6R by Beckman Coulter, Inc., Indianapolis, Ind., at 3000 rpm for 10 minutes and then the material was collected as a "pellet" after discarding the fluid. The pellet was then washed using ultrapure water twice with 10 minutes each in the same way the detergent wash was conducted. In all the washing steps, the solution to tissue ratio used was 100 ml solution per gram of $CO_2$ processed dry tissue.

DISINFECTION: After pouring out the liquid, a disinfection solution having 80:20 water:ethanol (200 proof) with 0.15 percent peracetic acid was added into the tube and the tube was placed on the orbital shaker to shake for 30 minutes and then centrifuged and washed in water for 20 minutes followed by washing in DPBS for 20 minutes to neutralize.

DECELLULARIZATION: The decellularizatiuon was performed in the same 500 ml centrifuge tube. The tissue was immersed in a 0.1 N NaOH solution for at least 19 hours followed by three short DPBS washes with 20 minutes each wash and 10 minutes spin (centrifugation). The tissue was then placed in 1M NaCl solution (in the 500 ml centrifuge tube) for a 20 minutes wash, following which the tissue was washed with ultrapure water (four times, 10 minutes each wash). The solution to tissue ratio maintained at 100 ml per gram of initial $CO_2$ processed dry weight for all the decellularization washes. After straining out the water, the tissue was lyophilized using a two-day drying cycle, after which a dry acellular omentum biomatrix was obtained. The lipid analysis using an FTIR method described in Example 1 showed that the material had very low residual lipid level (0.05 wt percent). Residual DNA testing was performed using the same method as describe in Example 3 showed that the material had low levels of residual DNA (0.006 wt. percent). Histology results (by HE staining) also showed that there were no cellular remnants in the material.

Example 6

Polydioxanone (PDO) Mesh Fabrication

Polydioxanone (PDO) mesh was obtained from Secant Medical (Perkasie, Pa.). The PDO mesh was prepared by taking 6-0 PDO fiber and back wounding onto the appropriate amount of spools needed to create the warp beams for knitting. These spools were then setup on a creel for warping after which, the spin finish was applied. Each fiber end was then threaded through a set of warping reeds and then over a rolling applicator prior to being placed onto the warp beam. The rolling applicator, containing a basin with the spin finish solution, was set at a controlled rate to ensure uniform application finish. From warping, the beams were then sent down to knitting and set up on the machine in the specific configuration needed to make the mesh. The ends were then threaded through the machine and the final settings were adjusted before the knitting was started. Once the full quantity of material was knit, it was transferred to a cutting process in which the knit roll was cut to fit onto the pinframes. The pinframes were then sent to an inert gas oven (nitrogen purged) and heated for 15 mins at 95° C. After heat-setting, the panels were then removed from the pinframes and cut into the final 7"×9" dimension. The final mesh units were then transferred to scouring where they were subjected to a 99 percent isopropyl alcohol solution in water to remove all of the applied spin finish. This step was repeated for a total of three washes. The panels were tested for physical characteristics (WPI:15; CPI:40; density: 0.014 $g/cm^2$; thickness: 0.635 mm) and then vacuum sealed in foil packages. FIG. 1 shows an image of the final PDO mesh.

Example 7

Preparation of the Absorbable Mesh-Reinforced Acellular Omentum Biomatrix

Figure 2:
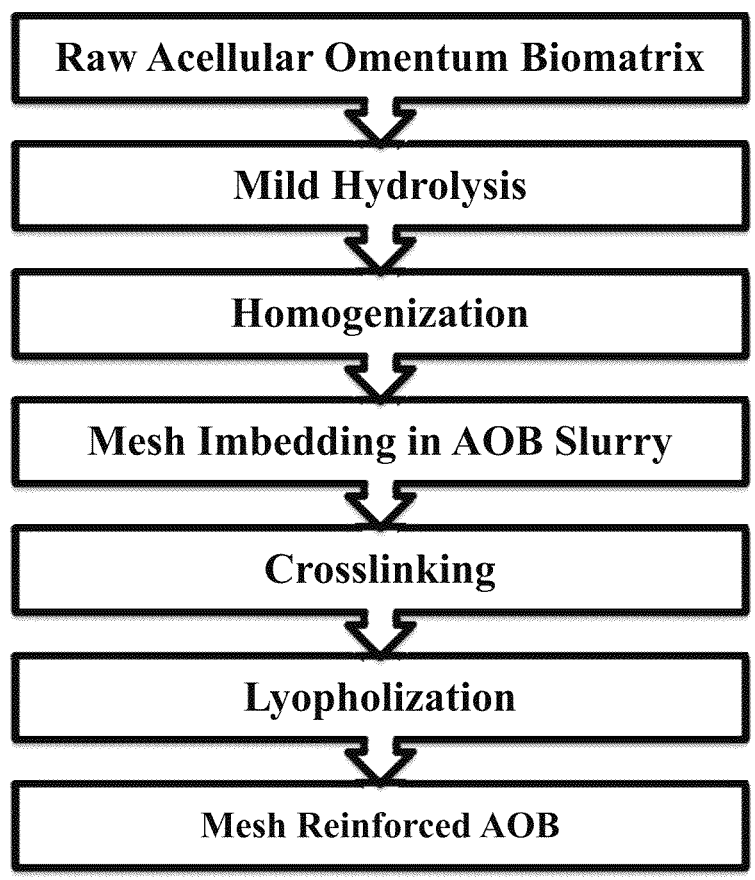
FIG. 2. Flowchart depicting the formulation of the mesh-reinforced acellular omentum biomatrix.

For the preparation of the mesh-reinforced acellular omentum biomatrix (AOB), the process shown in the flowchart in FIG. 2 was used. First, AOB prepared as described in Example 4, was placed in 0.01N HCl solution at a concentration of 12 mg/ml for one hour. The AOB suspension was then transferred into a stainless steel homogenizer and homogenized at low speed for 30 seconds to 1 minute. This was repeated for a total of 3 cycles. The homogenized AOB slurry was then transferred to a stainless steel tray (5"×5"). The AOB slurry was leveled using a spatula to ensure an even height distribution of the AOB (approximately 1.5 mm). The pre-framed (frame size ~4"×4") absorbable mesh was then carefully placed flat on the AOB layer. To complete the embedding process, the same homogenized slurry of AOB introduced to the bottom of the mold was also introduced to the top of the mesh, making sure the mesh was immersed in AOB material while keeping the mesh and AOB slurry well dispersed within the mold. Next, the mold was placed in a lyophilizer and lyophilized using the cycle shown in Table 1. Upon completion of the cycle, the mold was removed from the freezer dryer and the mesh-reinforced AOB sheet was carefully removed. The mesh-reinforced AOB samples were stored in a nitrogen gas box at room temperature until further processing or later use.

Figure 3:
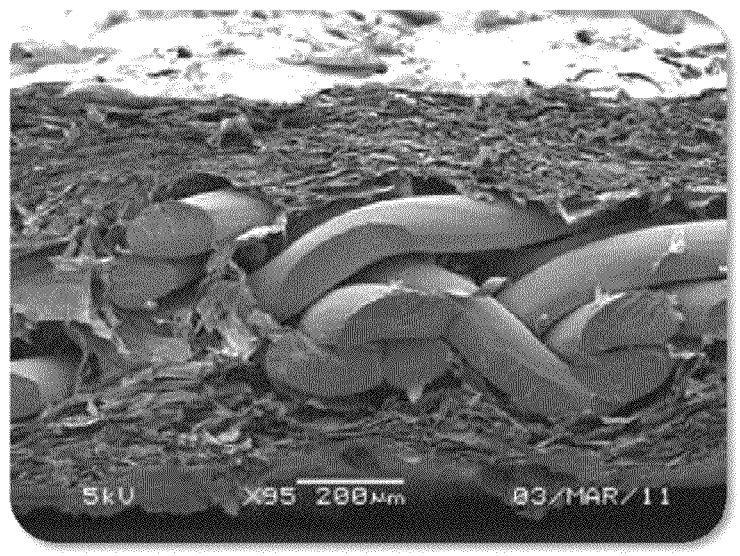
FIG. 3. Scanning electron microscopy image of the mesh-reinforced acellular omentum biomatrix.

To enhance the stability of the mesh-reinforced AOB samples, crosslinking was performed by soaking the mesh-reinforced AOB, made as described in this example, in 1 mg/ml 1-ethyl-3-(3-dimethyl aminopropyl)carbodiimide hydrochloride (EDC) (in 70 percent-90 percent alcohol) for 4 hours followed by rinsing with water for a total of three rinse cycles. To dry, the crosslinked sample was lyophilized following the cycle shown in Table 1. FIG. 3 depicts a scanning electron microscopy image, which shows the mesh reinforced crosslinked AOB composition.

The same procedures can be used to prepare non-absorbable mesh-reinforced acellular omentum biomatrix (AOB).

Example 8

Formulation of Acellular Omentum Biomatrix Scaffolds

For the preparation of the acellular omentum biomatrix (AOB) scaffold, AOB was prepared using the method as described in Example 3, then was placed in 0.01N HCl solution at a concentration of 10 mg/ml for one hour. The AOB suspension was homogenized. The homogenized AOB slurry was transferred to a stainless steel tray. The AOB slurry was then leveled using a spatula to ensure an even height distribution of the AOB. Next, the mold was placed in a lyophilizer and lyophilized using the cycle shown in Table 1. Upon completion of the cycle, AOB scaffold was carefully removed to yield non-crosslinked AOB scaffold. The non-crosslinked AOB scaffold was cut into discs having a diameter of 8 mm using a biopsy punch which were then sterilized by ebeam radiation at a dosage of 25 KGy.

Crosslinked AOB scaffold was prepared by soaking the non-crosslinked AOB scaffold (described above) in 1 mg/ml 1-ethyl-3-(3-dimethyl aminopropyl) carbodiimide hydrochloride (EDC) (in 70 percent-90 percent alcohol) for 4 hours. The crosslinked AOB scaffold was lyophilized following the cycle shown in Table 1. The crosslinked AOB scaffold was cut into discs having a diameter of 8 mm using a biopsy punch which were then sterilized by ebeam radiation at a dosage of 25 KGy.

Example 9

Rat Myocardial Infarction Study

Adipose derived stem cells (ADSCs) were used to demonstrate the utility of AOB scaffolds for stem cell delivery and its potential application for cardiac infarction treatment. Subcutaneous adipose tissue was acquired from the inguinal region of rat and digested to obtain a stromal vascular fraction. Briefly, the adipose tissue was washed with phosphate-buffered saline (PBS) and then treated with an enzyme solution comprised of 0.1 percent collagenase and 0.05 percent trypsin in PBS for 60 min at 37 degrees Celsius to release the cells. The released cells were collected by centrifugation and then resuspended in a-MEM sold under the tradename GIBCO by Life Technologies Corporation, Grand Island N.Y. supplemented with 10 percent FBS and plated onto cell culture dishes. The cells were trypsinized with 0.25 percent trypsin/0.04 percent EDTA (v/v 1:1) and passaged at a ratio of 1:3. The resultant adipose derived stem cells (ADSCs) were multipotent as judged by their ability to differentiate into adipocytes and osteoblasts.

The Rat ADSCs (Passage 4-6) were seeded on crosslinked and non-crosslinked AOB scaffolds, prepared as described in Example 8, at a density of 5 million cells per disc as cell graft.

A rat myocardial infarction model was used to evaluate the effect of AOB scaffolds with and without ADSCs on the Infarct size.

Myocardial infarction was induced by the ligation of the left anterior descending coronary artery (LAD ligation). Two weeks after LAD ligation, a left lateral thoracotomy was performed again, and the treatment was applied (see treatment groups below) to the infarct area of rat hearts and fixed by suturing with a 6-0 PROLENE® suture. The chest was then closed. The rats were maintained on standard rat chow and water ad libitum. Four treatment groups were included in this study:

Group I: animals with LAD ligation treated with suture only (sham AOB);
Group II: animals with LAD ligation treated with AOB scaffold (non-crosslinked) without cells;
Group III: animals with LAD ligation treated with AOB scaffold (cross-linked) without cells;
Group IV: animals with LAD ligation treated with $5 \times 10^6$ rat ADSCs seeded on cross-linked AOB scaffold;

At 1 week, 2 weeks, and 4 weeks after transplantation, the animals were euthanized with an overdose of sodium pentobarbital. Hearts were harvested and fixed in neutral buffered 4 percent formaldehyde for 48 h, and then subjected to histological analysis. At each time point, five sections were prepared at 5 different transversal levels encompassing the entire infracted area. The sections were stained with Masson's Trichrome and evaluated using computer assisted planimetry. The infarct size was quantified as the percentage of the total endocardial circumference of left ventricle occupied by the infracted endocardial circumference. Four weeks after transplantation, the infarct size in Group I was $56.2 \pm 4.1$ percent. The infarct size in Group II was $51.5 \pm 3.6$ percent. The infarct size in Group III was $48.5 \pm 3.2$ percent. The infarct size was reduced to $29.4 \pm 3.0$ percent in Group IV. No significant difference was observed between Group I, Group II and Group III ($p > 0.05$). Group IV had a statistically significant reduction in infarct size compared to Group I, Group II and Group III ($p < 0.01$, respectively).

We claim:

1. A method of delipidizing an omentum, the method comprising:
   (i) freeze-drying an omentum;
   (ii) heating the freeze-dried omentum to a temperature in the range of about 37° C. to about 40° C.;
   (iii) compressing the heated omentum to express fats and other lipids, thereby yielding a partially-delipidized omentum, wherein the step of compressing the heated omentum comprises gradually increasing the force of compression to at least about 22,000 lbs.; and
   (iv) contacting the partially-delipidized omentum with an extraction solvent to extract therefrom at least some of the remaining fats and other lipids, wherein (A) the extraction solvent is selected from the group consisting of hexane, cyclohexane, xylene, benzene, toluene, ethyl acetate, acetone, dioxane, acetonitrile, and combinations thereof, or (B) the extraction solvent is supercritical carbon dioxide.

2. The method of claim 1, further comprising, before step (i), mechanically processing the omentum into a plurality of pieces having a longest dimension in the range of about 1 mm to about 5 mm.

3. The method of claim 1, further comprising, before step (ii), mechanically processing the freeze-dried omentum into a plurality of pieces having a longest dimension in the range of about 1 mm to about 5 mm.

4. The method of claim 1, wherein the extraction solvent is selected from the group consisting of hexane, cyclohexane, xylene, benzene, toluene, ethyl acetate, acetone, dioxane, acetonitrile, and combinations thereof.

5. The method of claim 1, wherein the extraction solvent is supercritical carbon dioxide.

6. The method of claim 1, wherein step (iv) comprises:
   (1) contacting the partially-delipidized omentum with a polar solvent selected from the group consisting of acetone, dioxane, acetonitrile, and combinations thereof;
   (2) thereafter, contacting the partially-delipidized omentum with a first solvent mixture comprising both the polar solvent and a non-polar solvent selected from the group consisting of hexane, cyclohexane, xylene, benzene, toluene, ethyl acetate, and combinations thereof, wherein (A) the concentration of the polar solvent is about 30% to about 50% by weight of the first solvent mixture and (B) the concentration of the non-polar solvent is about 50% to about 70% by weight of the first solvent mixture; and
   (3) thereafter, contacting the partially-delipidized omentum with a second solvent mixture comprising both the polar solvent and the non-polar solvent, wherein (A) the concentration of the polar solvent is about 10% to about 30% by weight of the second solvent mixture and (B) the concentration of the non-polar solvent is about 70% to about 90% by weight of the second solvent mixture.

7. The method of claim 6, wherein the polar solvent is acetone and the non-polar solvent is cyclohexane.

8. The method of claim 7, wherein the weight ratio of the partially-delipidized omentum to the polar solvent in step (iv)(1) is about 1:3 to about 1:50, the weight ratio of the partially-delipidized omentum to the first solvent mixture in step (iv)(2) is about 1:3 to about 1:50, and the weight ratio of the partially-delipidized omentum to the second solvent mixture in step (iv)(3) is about 1:3 to about 1:50.

9. The method of claim 1, further comprising, as step (v), rehydrating the delipidized omentum.

10. The method of claim 9, further comprising, as step (vi), decellularizing the rehydrated delipidized omentum.

11. The method of claim 10, further comprising, as step (vii), disinfecting the decellularized omentum.

12. The method of claim 11, wherein step (vii) further comprises sterilizing the decellularized omentum.

13. A construct for medical purposes comprising an omentum processed in accordance with the method of claim 12.

14. A method of making a foam decellularized delipidized omentum, the method comprising:
   providing an omentum processed in accordance with the method of claim 12;
   preparing a suspension of the omentum in 0.1N HCl;
   homogenizing the suspension into an omentum slurry;
   pouring the omentum slurry into a mold;
   placing the mold containing the omentum slurry into a lyophilizer; and
   lyophilizing the omentum slurry, yielding the foam decellularized delipidized omentum.

15. The method of claim 14, further comprising crosslinking the foam decellularized delipidized omentum.

16. The method of claim 14, further comprising placing a woven or nonwoven mesh in the mold prior to or partway through pouring the omentum slurry into the mold.

17. A foam decellularized delipidized omentum prepared in accordance with the method of claim 14 or claim 15.

18. A mesh-reinforced omentum prepared in accordance with the method of claim 16.

19. A method of treatment of myocardial infarction comprising:
   providing a foam decellularized delipidized omentum prepared in accordance with the method of claim 14 or claim 15;

seeding the foam decellularized delipidized omentum with adipose-derived stem cells;
accessing a heart having an infarct area; and
applying the adipose-derived stem cell seeded foam decellularized delipidized omentum to the infarct area.

* * * * *